United States Defensive Publication [19] (H) [11] T980,004

Osborn [43] Mar. 6, 1979

[54] PHENOLIC DYE-FORMING COUPLERS

[75] Inventor: Harland J. Osborn, Rochester, N.Y.

[73] Assignee: Eastman Kodak Company, Rochester, N.Y.

[21] Appl. No.: 874,164

[22] Filed: Feb. 1, 1978

Related U.S. Application Data

[62] Division of Ser. No. 774,087, Mar. 3, 1977, Pat. No. 4,124,396.

[51] Int. Cl.[2] ..... C07C 143/75; C07C 143/79

[52] U.S. Cl. ..... 260/556 A; 260/307 B; 260/307 D; 260/308 R; 260/308 A; 260/308 D; 260/401; 260/556 S; 260/556 AR

[57] ABSTRACT

2,5-Dicarbonylaminophenols containing a p-alkylsulfonylaminophenoxy terminal moiety or a p-alkylaminosulfonylphenoxy terminal moiety in the five-position substituent of the molecule are color-forming couplers useful in photographic silver halide emulsions and elements.

4 Claims, No Sheets Drawing,

28 Pages Specification

The file of this unexamined application may be inspected and copies thereof may be purchased (849 O.G. 1221, Apr. 9, 1968).